US005779867A

United States Patent [19]

Shieh

[11] Patent Number: 5,779,867
[45] Date of Patent: *Jul. 14, 1998

[54] DRY CHEMISTRY GLUCOSE SENSOR

[75] Inventor: Paul Shieh, Fremont, Calif.

[73] Assignee: Biomedix, Inc., Fremont, Calif.

[*] Notice: The term of this patent shall not extend beyond the expiration date of Pat. No. 5,522,977.

[21] Appl. No.: 657,763

[22] Filed: May 31, 1996

Related U.S. Application Data

[63] Continuation-in-part of Ser. No. 319,618, Oct. 7, 1994, Pat. No. 5,522,977.

[51] Int. Cl.$^6$ .................................. G01N 27/327
[52] U.S. Cl. ................. 204/403; 204/418; 205/777.5; 435/817; 436/807
[58] Field of Search .................. 204/418, 403; 205/777.5; 435/817; 436/807

[56] References Cited

U.S. PATENT DOCUMENTS

| | | | |
|---|---|---|---|
| 4,406,770 | 9/1983 | Chan et al. | 204/415 |
| 4,897,173 | 1/1990 | Nankai et al. | 204/403 |
| 5,120,420 | 6/1992 | Nankai et al. | 204/403 |
| 5,149,630 | 9/1992 | Forrest et al. | 204/403 |
| 5,264,103 | 11/1993 | Yoshioka et al. | 204/403 |
| 5,334,296 | 8/1994 | Henkens et al. | 204/418 |
| 5,385,846 | 1/1995 | Kuhn et al. | 204/403 |
| 5,522,977 | 6/1996 | Shieh | 204/418 |

*Primary Examiner*—T. Tung
*Attorney, Agent, or Firm*—Marvin S. Aronoff

[57] ABSTRACT

A self contained glucose sensor is provided that generally comprises a strip type glucose sensing electrode having an active surface comprising an organic conducting redox salt dispersed in a polymeric membrane, with the membrane coating a conductive strip and a strip type Ag/AgCl reference electrode having its active surface separated from physical contact with the strip type glucose sensor and a carrier strip of water absorbent paper or film containing an enzyme system and an oxidizable dye. The water absorbent carrier strip is in simultaneous contact with both the active surface of the strip type glucose electrode and the active surface of the strip type reference electrode. When an aqueous solution containing glucose is brought in contact with the carrier strip containing the enzyme system an electrical potential, proportional to the concentration of glucose in the solution, is created which can be detected by an electrometer or other suitable device.

13 Claims, 1 Drawing Sheet

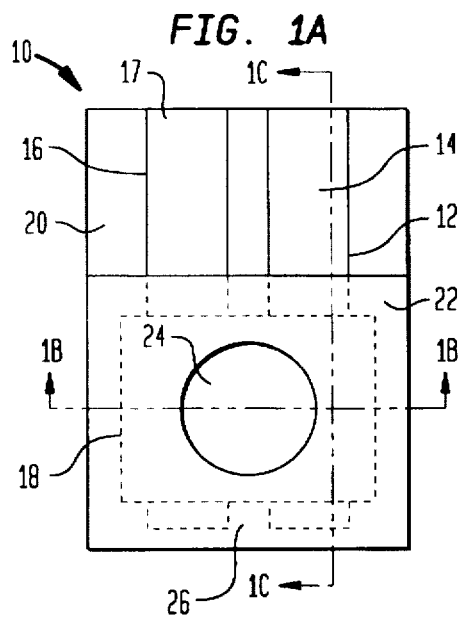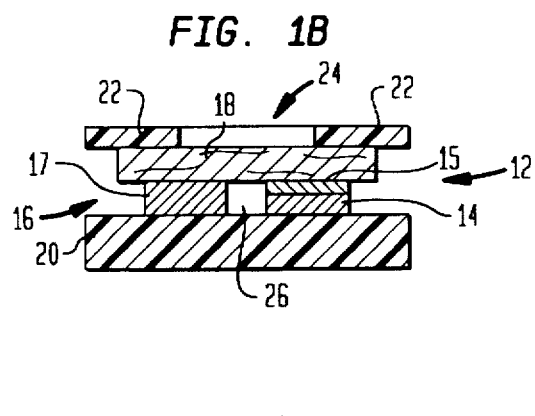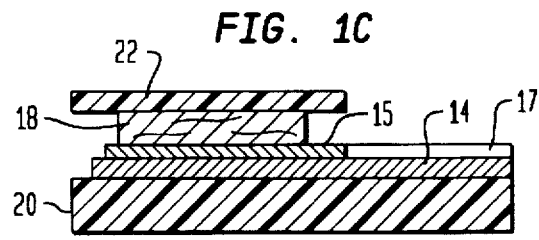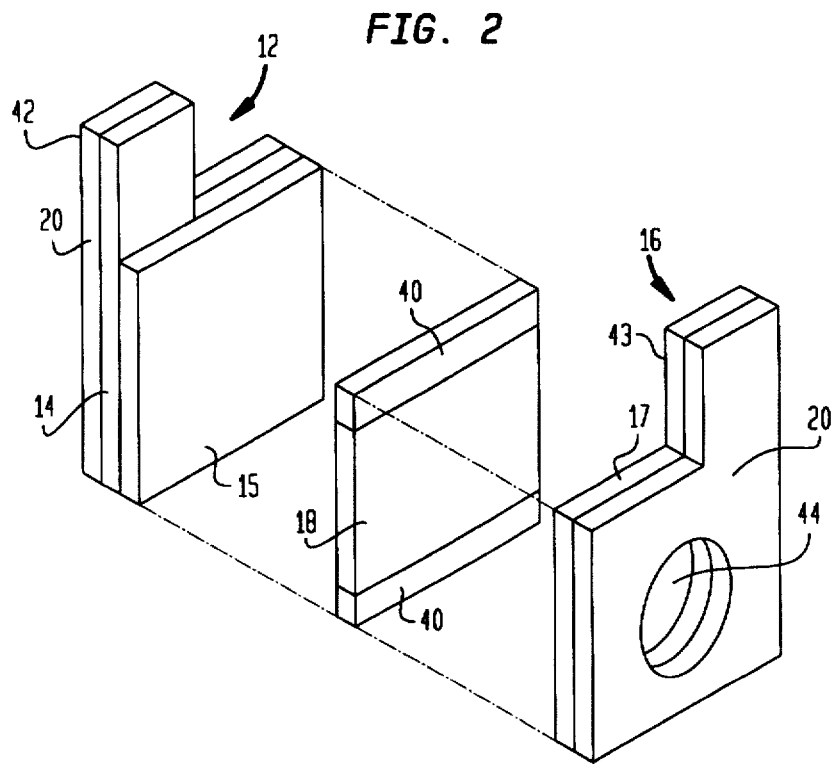

DRY CHEMISTRY GLUCOSE SENSOR

CROSS REFERENCE TO RELATED APPLICATION

This application is a continuation in part under rule 37 CFR 1.53 of U.S. patent application Ser. No. 08/319618, now U.S. Pat. No. 5,522,977, filed Oct. 7, 1994, and entitled Glucose Sensor.

BACKGROUND OF THE INVENTION

Although there are numerous methods for the quantitative determination of glucose in biological fluids, there is a need for a simple, rapid, highly sensitive, accurate and reproducible means which can be easily miniaturized, inexpensively produced, and which is inexpensive to use. Such means would be especially useful, convenient and less painful to the patient when screening for and monitoring diabetes in the human if only a few drops of blood were required for a reliable test. The usefulness of such means would be enhanced if it had sufficient sensitivity and accuracy to be applied to the quantitative determination of glucose concentrations in urine, which generally are far lower than in the blood. In addition, a simple, rapid, economical and convenient means which can be applied to the on-site monitoring of glucose concentrations during food processing and in agricultural products is needed. Furthermore, there is a need to increase the convenience and rapidity of glucose assays and to reduce the possibility of inaccurate results due to operator error in the preparation and use of aqueous solutions, by eliminating the need to prepare or mix such solutions prior to performing the assay.

For the foregoing reasons there is a need for a device for the quantitative assay of glucose in biological and other fluids which is simple to use, eliminates the need to prepare test solutions, delivers the assay rapidly, is highly sensitive, accurate and reproducible, and which can be easily miniaturized, inexpensively produced and inexpensively used. Preparation of a glucose sensor using a plasticized PVC membrane containing a complex of TTF and TCNQ and the use of the sensor in a glucose assay method which requires the preparation of aqueous solutions is disclosed in U.S. patent application Ser. No. 08/319618, filed Oct. 7, 1994. The disclosure of this application is hereby incorporated by reference.

BRIEF DESCRIPTION OF THE INVENTION

The present invention is directed to providing a conveniently assembled, self contained sensor for the assay of glucose, based on the generation of a potential change proportional to the concentration of glucose in a solution to which the cell is exposed.

A further object of the present invention is to provide a redox electrode with high sensitivity and rapid response which in conjunction with an external enzyme system in easily useable form provides an improved means for detection of glucose in biological fluids such as human blood or urine.

Yet another object of the present invention is to provide a self contained sensor for detection of glucose in biological fluids that may be readily miniaturized, is easy and economical to manufacture and may be incorporated in diagnostic kits or used as a component of an automated system.

The above and other objects are achieved in accordance with the present invention by providing a self contained potentiometric cell comprising a strip type glucose sensor; the sensor having an active surface comprising an organic conducting redox salt dispersed in a polymeric membrane which coats a conductive strip; a strip type reference electrode having its active surfaces separated from physical contact with the strip type glucose sensor; and a carrier strip of water absorbent paper or film containing a formulation of an enzyme system and an oxidizable dye, the water absorbent paper or film in simultaneous physical and electrical contact with both the active surface of the strip type glucose detector and the active surface of the strip type reference electrodes, so that when an aqueous solution containing glucose is brought in contact with the paper or film containing the enzyme system a potential, proportional to the concentration of glucose in the solution, is created between the strip type glucose sensor and the reference electrode.

An embodiment of the self contained glucose sensor of the present invention comprises a glucose sensor comprising a polymeric base strip having a thin layer of a conductive graphite formulation such as ERCON G-448(I) Graphite, available from ERCON Inc., Watham, Mass., with the conductive graphite coated with a sensing membrane, the membrane made of plasticized PVC containing a TTF/TCNQ complex made by mixing equal parts by weight of TTF and TCNQ in a solvent and concentrating the solution in the presence of an undissolved particle of TCNQ to form a burgundy-red solution. The embodiment further comprises an Ag/AgCl reference electrode strip prepared by coating a base support such as polyester film with a conductive Ag/AgCl conductive formulation such as ERCON R-421 (DBE-60) Silver/Silver Chloride and curing the coating for about one hour at about 70° C.

The embodiment still further comprises a carrier containing a formulation comprising an enzyme system and an oxidizable dye for the detection of glucose. The carrier is prepared by soaking a water absorbent strip, such as a paper strip with an aqueous solution, buffered to pH 6.8, containing the enzymes glucose oxidase and peroxidase, tetramethylbenzidine dihydrochloride, gelatin, methocel and cholic acid and then drying the strip to constant weight. The cell is formed by placing the carrier containing the formulation comprising the enzyme system and oxidizable dye in simultaneous contact with the glucose sensor and reference electrode. A glucose containing solution which is then applied to the carrier paper produces a potential change between the electrodes that is related to the concentration of glucose and which may be detected by suitable means.

BRIEF DESCRIPTION OF THE DRAWINGS

FIG. 1A is an overview of a self contained glucose sensor.

FIG. 1B is a cross-sectional view of the self contained glucose sensor.

FIG. 1C is a cross-sectional view of the sensing electrode.

FIG. 2 is an exploded view of a self contained glucose sensor having a sandwich configuration.

DESCRIPTION OF THE PREFERRED EMBODIMENTS

The following abbreviations used in the description of different embodiments of the invention are hereby defined:

TCNQ—7,7,8,8-Tetracyanoquinodimethane

TTF—Tetrathiafulvalene

TMB—3,3',5,5'-Tetramethylbenzidine dihydrochloride

THF—Tetrahydrofuran

PVC—Polyvinylchloride

GOX—Glucose oxidase
POX—Horseradish peroxidase
CA—Cholic acid, sodium salt
MET—Methocel 40-101(Dow Chemical Co., Midland, Mich.)
GEL—Gelatin FIG. 1A is an overall view of an embodiment of a self contained glucose sensor used to assay glucose. FIG. 1B is a cross-sectional view of the same along line A—A of FIG. 1A. FIG. 1C is a cross-sectional view along line B—B of FIG. 1A and depicts a sensing electrode also referred to as a redox electrode or glucose sensing electrode.

The self contained glucose sensor 10 comprises a non-conductive base 20, a sensing electrode 12 which is a strip type redox electrode having a redox membrane 15, a reference electrode 16, which is a strip type electrode, with the sensing electrode 12 separated from reference electrode 16 by a gap 26, and a carrier strip 18, containing enzymes and an oxidizable dye, with the carrier strip 18, in simultaneous contact with redox membrane 15 and reference electrode 16, and a cover 22, having opening 24 through which a sample may be introduced.

The sensing electrode 12 comprises a conductive coating 14 coated on non-conductive base 20, with at least a portion of the surface of conductive coating 14 coated with redox membrane 15. Redox membrane 15 is generally a polymeric membrane and contains a complex of TTF and TCNQ. The complex of TTF and TCNQ characterized by a burgundy red coloration and having an ultraviolet absorption spectrum with broad absorption from about 340 nanometers to about 550 nanometers and formulated in the manner described in U.S. patent application Ser. No. 08/319,618 is preferred. In practice, electrically conductive coating 14 is comprised of conductive carbon, but copper, silver, gold, aluminum, platinum, nickel, stainless steel, iron and other conductive materials and mixtures or coatings thereof can be used. Conductive carbon is preferred for the coating 14 with conductive graphite more preferred and conductive formulations such as ERCON G-448(I) Graphite (available from ERCON Inc., Watham, Mass.), most preferred.

The reference electrode 16 is generally also a strip electrode comprising a conductive layer of a reference electrode formulation 17 on non-conductive base 20. An Ag/AgCl strip reference electrode is generally preferred as this may be conveniently prepared from commercially available formulations such as a polymeric Ag/AgCl ink, ERCON R-421 (DBE-60) Silver/Silver Chloride, (Ercon Inc., Waltham Mass.). However, other types of reference electrodes such as a standard calomel electrode may also be used, providing that they have an active surface which can be brought into electrical contact with carrier strip 18.

FIG. 2, is an exploded view of a version of the self contained glucose sensor having a sandwich configuration. The self contained glucose sensor generally comprises a sensing electrode 12, a reference electrode 16 and a carrier strip 18. Sensing electrode 12 further comprises a non-conductive base 20 coated with a conductive coating 14 with the surface of conductive coating 14 coated with redox membrane 15. Reference electrode 16 further comprises a non-conductive base 20. In the version of the sensor depicted in FIG. 2, the sensing electrode 12 has a conductive protrusion 42 and reference electrode 16 has a conductive protrusion 43. Protrusions 42 and 43 are not in contact and serve as convenient points for electrical connection. Carrier strip 18 is sandwiched between sensing electrode 12 and reference electrode 16 and is in simultaneous contact with redox membrane 15 of sensing electrode 12 and the electrically conductive layer 17 of reference electrode 16. The sandwich configuration may be optionally held together by clamps, tape and the like. Optionally, spacers 40 may be used to keep sensing electrode 12 and reference electrode 16 physically separated. Spacers 40 may comprise any non-conductive adhesive means, such as adhesives and double sided adhesive tape.

The sensing electrode 12 and the reference electrode 16 in practice are electrically connected to form an electrical circuit through an electrometer or other voltage sensing device. The reference electrode 16 is typically silver-silver chloride.

Carrier strip 18 comprises a porous matrix, typically a paper, membrane or film, containing an enzyme system and an oxidizable dye. A porous or fibrous matrix that is a water absorbent strip is preferred for carrier strip 18 as it can be impregnated with aqueous solutions containing an enzyme system and an oxidizable dye and will readily absorb aqueous assay samples containing glucose. Any water absorbent porous matrix, in practice a membrane or paper or paper-like material whether cellulosic, non-cellulosic or a mixture of cellulosic and non-cellulosic components that can be impregnated with the enzyme mixture, oxidizable dye formulation can be used as a carrier. However, water absorbent porous matrices, typically membranes and papers, that produce a linear correlation of potential change with glucose concentration or that produce greater sensitivity and reproducible results with glucose concentration are preferred for the carrier strip. Examples of such water absorbent matrices, membranes and papers are Brawny™ 2-ply paper towel (James River Corp., Norwalk, Conn.); Baxter S/P qualitative filter paper Grade 360; Loprosorb™ or LoProdyne™ Nylon 66 (Pall Biosupport, East Hills, N.Y.); Biodyne® A ampho-teric Nylon 66 membrane (Pall); Leukosorb™ Type A and Leukosorb™ Type B polyester (Pall).

The water absorbent film or paper comprising water absorbent carrier strip 18 is impregnated with an enzyme system, oxidizable dye formulation. The enzyme system, oxidizable dye formulation generally comprises an aqueous mixture having the following composition: GOX about 5 Units/ml to about 1200 Units/ml, with about 20 Units/ml preferred; horseradish peroxidase about 200 Units/ml to about 800 Units/ml, with about 400 Units/ml preferred; an oxidizable dye such as TMB about 0.05% to about 2%, with about 0.25% preferred; a surfactant such as cholic acid, Triton X-100, polyethylene glycol, sodium lauryl sarcosinate and sodium lauryl sulfate or mixtures thereof about 0.05% to about 8%, with about 0.5% preferred; thickening agents such as gelatin and methocel and the like with about 0.01% to about 2% gelatin, with about 0.5% gelatin preferred; and 0% to about 1% Methocel, with about 0.5% Methocel preferred. Any water soluble or water dispersible aqueous thickening or gelling agent may be used in the carrier strip providing it does not interfere with the chemical processes which occur during glucose assay. Preferred quantities generally give a fast, reproducible response.

The following examples illustrate the construction and use of the self contained glucose sensor:

Example 1 describes preparation of a strip electrode using ERCON G-448(I) Graphite.

EXAMPLE 1

A layer of ERCON G-448(I) Graphite, was formed on Mylar® polyester film using a steel doctor knife having a 1 mil gap. The coated polyester film was then dried in an oven at 70° C. for 1 hour. Membrane forming solution containing burgundy red TCNQ-TTF complex was prepared as described in U.S. patent application Ser. No. 08/319,618. This solution was applied to the dried graphite surface with a steel doctor knife having a 2 mil gap. The coated graphite surface was then dried in an oven at 70° C. for 10 minutes. Working electrodes prepared in this manner were stored in closed containers at room temperature.

Example 2 describes preparation of a strip reference electrode.

EXAMPLE 2

Polymeric Ag/AgCl ink (ERCON R-421(DBE-60) Silver/Silver Chloride) was laid down on a polyester base support film (e.g. Mylar®) and spread with a steel doctor knife having about a 1 mil—about a 2 mil gap, to produce an evenly distributed thin layer. The Ag/AgCl coating was cured at 70° C. for one hour.

Example 3 describes preparation of an enzyme system for the detection of glucose in a carrier.

EXAMPLE 3

An enzyme solution for the detection of glucose was prepared by mixing 11.2 mg GOX (7.1 u/mg activity), 12.7 mg POX (126 u/mg), 10 mg TMB, 20 mg Gel, 20 mg Met 40-101 and 20 mg CA in 4 ml of a phosphate buffer solution having pH 6.8, a buffer capacity of 10 mM and containing 50 mM KCl. Prior to adding to this solution, TMB was dispersed in 0.5 ml of hot water.

Two strips of paper about 4×8 cm in size were immersed in this solution for 2 minutes, then transferred to a Teflon® sheet and dried in an oven at 40° C. for 30 minutes. This procedure was repeated to absorb any remaining solution on the paper strips. The paper strips were then redried in the oven at 40° C. to constant weight. The enzyme paper was placed in a closed container and stored in a freezer.

Example 4 shows how a self contained glucose sensor is formed from the sensing electrode, the reference electrode, and the enzyme containing paper.

EXAMPLE 4

The sensing electrode described in Example 1 and the Ag/AgCl reference electrode described in Example 2 were placed on a flat surface with their active surfaces exposed and were separated by a gap of 1-2 mm. A 1×0.8 cm strip of the enzyme paper prepared in Example 3 was placed on top of the active surfaces of the electrodes, so that it bridged the gap between them and formed a self contained glucose sensor. Electrical connection was made from the conductive surface of each electrode to an electrometer so that any potential changes in the cell could be monitored. To determine glucose concentration, a measured amount of liquid sample was applied to the enzyme paper, preferably in the zone between the electrodes. Glucose concentration was determined by voltage change as disclosed in U.S. patent application Ser. No. 08/319,618 filed Oct. 7, 1994.

EXAMPLE 4A

A version of the self contained glucose sensor illustrated in FIGS. 1A, 1B and 1C was prepared using the general techniques of Examples 1, 2, 3 and 4 except that the sensing electrode and the reference electrode were formed as adjacent strips on the surface of a single piece of polyester film. In addition, a cover was formed by placing over the carrier strip a strip of polyester film having a hole punched through it. Test solution was introduced through the hole in the cover.

EXAMPLE 4B

This example illustrates construction of a version of a self contained glucose sensor having a sandwich configuration. This is seen in exploded view in FIG. 2, in which reference electrode 16 and sensing electrode 12 form the "bread" of the sandwich and carrier strip 18 and spacers 40 comprise the "filling" of the sandwich. Protrusion 42 and protrusion 43 are arranged so that they protrude from the same side of the sandwich. However, protrusions 42 and 43, which are used for electrical connection, do not come into physical contact. Protrusion 42 of sensing electrode 12 may or may not be coated with redox membrane 15. A sensing electrode was prepared using the technique of Example 1 and a reference electrode was prepared on a separate piece of polyester film using the technique of Example 2. A hole was punched out through a section of the reference electrode to form opening 44. Double sided adhesive tape (e.g. 3M #415 and 465; and ARcare® #7148, 7840 and 7841 (Adhesives Research Inc., Glen Rock, Pa.) was applied to the active surface of the reference electrode in two areas adjacent to the punched out hole and opposite each other to serve as spacers 40. A piece of carrier strip 18 prepared as in Example 3 was placed over the punched out hole 44 and in contact with conductive layer 17 between the two pieces of double sided tape. Sensing electrode 12 was placed over reference electrode 16 so that its protrusion 42 protruded from the same side of the sandwich as protrusion 43, as indicated in FIG. 2.

However, other configurations in which the protrusions are aligned differently can be used in situations where this is more convenient. The sensing electrode was positioned so that its active surface 15 made contact with the carrier strip. Sensing electrode 12 was then pressed down, so that it adhered to the double faced tape, forming a sandwich, in which the active surfaces faced each other and the reagent strip was sandwiched between the active surfaces and was in contact with them. Electrical connections were made to each electrode which were connected to an electrometer as described in Example 4. The test sample was applied to the carrier strip through the hole in the reference electrode.

EXAMPLES 5-11

Examples 5-11 are summarized in Table 1. In these examples glucose analysis was performed with self contained glucose sensors constructed with different commercially available papers as the enzyme carrier. Standard glucose solutions containing urea, (available from Sigma Chemical Co., St. Louis, Miss.) were used in each case. Glucose and urea concentrations for each standard solution in mg/dl were as follows: 50 and 5; 100 and 10; 200 and 30; 300 and 100. The results of Examples 5-11 indicate that the results are dependent on the type of paper employed as the enzyme carrier. Papers similar in type to "Brawny" paper and Loprosorb are generally preferred as they produce a linear relationship between the logarithm of glucose concentration and measured sensor potential with good sensitivity.

TABLE 1

Glucose sensor performance with various enzyme reagent strip carrier materials

| | | Sensor response, mV Glucose Concentration (Urea Conc.)* | | | | | Response | |
|---|---|---|---|---|---|---|---|---|
| Example | Reagent strip | 50 (5) mg/dl | 100 (10) mg/dl | 200 (30) mg/dl | 300 (100) mg/dl | Sensitivity** $\Delta$ mV/mg/dl | time, sec. | Linearity*** |
| 5 | Brawny paper towel | 239 | 275 | 322 | 368 | 0.52 | 30 | + |
| 6 | Rainbow paper towel | 318 | 281 | 420 | 478 | 0.64 | 20 | − |
| 7 | Baxter filter paper | 218 | 233 | 267 | 322 | 0.41 | 30 | ± |
| 8 | Ultipor fiber glass | 289 | 294 | 360 | 342 | 0.21 | 30 | − |
| 9 | Loprosorb | 265 | 285 | 294 | 312 | 0.19 | 30 | + |
| 10 | Leukosorb A | 226 | 211 | 292 | 290 | 0.26 | 20 | − |
| 11 | Leukosorb B | 253 | 259 | 265 | 276 | 0.09 | 20 | ± |

*glucose/urea standard solutions from Sigma Chemical Co.
**based on reading at 300 mg/dl − reading at 50 mg/dl
***+ = linear response;
− = non-linear response;
± = marginally linear response

EXAMPLES 12–14

Examples 12–14 are summarized in Table 2. In these examples, glucose analysis was performed with self contained glucose sensors in which "Brawny" 2-ply paper towel (James River Corp., Norwalk Conn.) was employed as the enzyme carrier. Potentiometric measurements were made over a range of glucose concentrations on glucose solutions, glucose solutions containing urea and glucose in artificial serum having the composition: calcium chloride 0.51 mM, dibasic ammonium phosphate 0.47 mM, magnesium chloride 0.16 mM, sodium chloride 14 mM, potassium chloride 0.51 mM, urea 0.03 mM. These measurements demonstrate that a rapid, linear response is obtained for a range of glucose concentrations in each case although there are slight changes in performance (i.e. observed potential) at high glucose concentrations.

TABLE 2

Glucose sensor performance with various glucose standards.

| | | Sensor response[a], mV | | | | | Response | |
|---|---|---|---|---|---|---|---|---|
| Example | Sample | 50[b] mg/dl | 100[b] mg/dl | 200[b] mg/dl | 300[b] mg/dl | Sensitivity, mV/mg/dl | time, sec. | Linearity |
| 12 | Glucose standard[c] | 240 | 261 | 297 | 350 | 0.44 | 20 | + |
| 13 | Glucose standard with urea[d] | 239 | 275 | 322 | 368 | 0.52 | 30 | + |
| 14 | Glucose standard in artificial serum[e] | 227 | 285 | 310 | 332 | 0.42 | 20 | + |

[a]sensor with Brawny reagent strip paper
[b]glucose concentration
[c]from Sigma
[d]from Sigma. Urea nitrogen concentrations: 5 mg/dl (1.79 mM), 10 mg/dl (3.57 mM), 30 mg/dl (10.71 mM), 100 mg/dl (35.7 mM) at 50, 100, 200, 300 mg/dl respectively
[e]prepared in-house, glucose concentrations tested are: 66, 116, 216 and 316 mg/dl

EXAMPLES 15–18

Examples 15–18 are summarized in Table 3. In these examples, glucose analysis was performed with self contained glucose sensors constructed with different commercially available papers as the enzyme carrier. Potentiometric measurements were made over a range of glucose concentrations in the presence of Sugar Chex®, a simulated whole blood standard (available from Streck Laboratories, Inc., Omaha, Nebr.) in order to calibrate the sensors under these conditions.

TABLE 3

Glucose sensor performance with various enzyme reagent strip materials and Sugar Chex ® whole blood standards.

| | | Sensor Response in mV to concentration of glucose in whole blood standard | | | | | |
|---|---|---|---|---|---|---|---|
| Example | Reagent strip | 52* mg/dl | 104* mg/dl | 206* mg/dl | 361* mg/dl | Sensitivity** mV/mg/dl | Linearity |
| 15 | Brawny paper | 165 | 187 | 238 | 204 | 0.47 | – |
| 16 | Biodyne A | 271 | 286 | 328 | 361 | 0.37 | + |
| 17 | Leukosorb A | 245 | 268 | 289 | 310 | 0.28 | + |
| 18 | Leukosorb B | 201 | 220 | 255 | 278 | 0.35 | + |

*Whole blood glucose standard concentration.
**Sensitivity value determined for concentrations between 52 and 206 mg/dl glucose only.

In terms of linearity and magnitude of potential response, the best results were obtained when Biodyne A (amphoteric Nylon 66) or Leukosorb A or B papers were used as the enzyme carrier under these conditions. These papers may be more efficient than "Brawny" in filtering particles of the simulated whole blood, since such particles may interfere with linear response. Under conditions where particulate matter is present, enzyme carriers having an effective pore size sufficient to filter out the particulate matter are preferred. When the glucose concentration of whole human or animal blood is being monitored, an enzyme carrier strip having an effective pore size sufficiently small to filter out formed bodies present in the blood is preferred. For human whole blood an effective pore size generally about 10 μM or smaller is preferred to obtain a linear response in the glucose assay.

The versions of the self contained sensor of the present invention provide compact, convenient, easily manufactured and inexpensive means for the assay of glucose which have high sensitivity and a rapid response. As the sensors of the present invention may be provided as assembled units containing the reagent strip for the assay of glucose, they eliminate the need to prepare and deliver solutions containing the reagents needed for glucose assay. Thus they save time, require little space for preparation and performance of the assay, eliminate mess and cleanup and eliminate error associated with the preparation and delivery of reagent solutions.

Although the present invention has been described in considerable detail with reference to certain preferred versions thereof, other versions are possible. For example, other versions of the sensor are possible as is its use in conjunction with instrumentation such as devices for determination of glucose in media such as biological fluids, foodstuffs and waste streams. Therefore, the spirit and scope of the appended claims should not be limited to the description of the preferred versions contained herein.

What is claimed is:

1. A self contained sensor for the potentiometric assay of glucose comprising:
   a sensing electrode strip, the sensing electrode strip comprising;
      an electrically insulating base strip and an electrically conductive layer in contact with the base strip and a redox membrane which coats the electrically conductive layer, the redox membrane comprising;
         a polymer matrix, the polymer matrix containing;
            a plasticizer, and
            a complex of 7,7,8,8-tetracyanoquinodimethane and tetrathiafulvalene characterized by a burgundy red coloration, and a reference electrode strip, the reference electrode strip comprising;
      an electrically insulating base strip coated with an electrically conductive formulation containing silver and silver chloride, with the reference electrode and the sensing electrode having a gap between them, and a water absorbent carrier strip, the water absorbent carrier strip impregnated with a mixture comprising;
         glucose oxidase,
         peroxidase,
         an oxidizable dye,
         at least one surfactant and
         at least one thickening agent, with the carrier strip bridging the gap between the sensing electrode strip and the reference electrode strip and in simultaneous contact with the redox membrane of the sensing electrode and the coating of electrically conductive formulation containing silver and silver chloride of the reference electrode.

2. The self contained sensor for the assay of glucose of claim 1 in which the electrically conductive layer of the sensing electrode comprises a conductive graphite formulation and the redox membrane comprises a matrix of polyvinylchloride.

3. The self contained sensor for the assay of glucose of claim 2 in which the water absorbent carrier strip comprises a porous matrix.

4. The self contained sensor for the assay of glucose of claim 3 in which the porous matrix has an effective pore size sufficiently small to filter out formed bodies present in human or animal blood.

5. The self contained sensor for the assay of glucose of claim 3 in which the porous matrix has an effective pore size of about 10 micrometers or less.

6. The self contained sensor for the assay of glucose of claim 3 in which the oxidizable dye is 3,3',5,5'-tetramethylbenzidine dihydrochloride.

7. The self contained sensor for the assay of glucose of claim 6 in which the at least one surfactant is chosen from the group consisting of cholic acid, Triton X-100, polyethylene glycol, sodium lauryl sarcosinate and sodium lauryl sulfate or mixtures thereof.

8. The self contained sensor for the assay of glucose of claim 7 in which the at least one thickening agent is chosen from the group consisting of gelatin, methocel or mixtures thereof.

9. The self contained sensor for the assay of glucose of claim 1 in which the sensing electrode strip and the reference electrode strip share a common electrically insulating base strip.

10. The self contained sensor for the assay of glucose of claim 1 in which the reference electrode strip has an opening and the carrier strip is sandwiched between and in simultaneous contact with the redox membrane of the sensing electrode strip and the coating of electrically conductive formulation containing silver and silver chloride of the reference electrode strip and the carrier strip is exposed through the opening in the reference electrode to enable a test sample to be introduced.

11. A potentiometric sensing electrode comprising:

an electrically insulating base strip and an electrically conductive layer in contact with the base strip and a redox membrane which coats the electrically conductive layer, the redox membrane comprising:

a polymer matrix, the polymer matrix containing:

a plasticizer, and a complex of 7,7,8,8-tetracyanoquinodimethane and tetrathiafulvalene characterized by a burgundy red coloration.

12. The sensing electrode of claim 11 in which the electrically conductive layer comprises a conductive graphite formulation.

13. The sensing electrode of claim 11 in which the redox membrane comprises a matrix of polyvinylchloride.

* * * * *